United States Patent [19]

Combs et al.

[11] Patent Number: 5,221,742

[45] Date of Patent: Jun. 22, 1993

[54] PROCESS FOR THE PREPARATION OF 6-(3,4-DIHYDRO-3-OXO-1,4(2H)-BENZOXAZIN-7-YL)-2,3,4,5-TETRAHYDROPYRIDAZIN-3-ONES

[75] Inventors: Donald W. Combs, Piscataway, N.J.; James P. Demers, New York, both of N.Y.

[73] Assignee: Ortho Pharmaceutical Corporation, Raritan, N.J.

[21] Appl. No.: 631,550

[22] Filed: Dec. 21, 1990

[51] Int. Cl.$^5$ .................. C07D 413/02; C07D 413/10
[52] U.S. Cl. .................................................... 544/105
[58] Field of Search ......................................... 544/105

[56] References Cited

U.S. PATENT DOCUMENTS 4,721,784  1/1988  Combs ................................ 544/105
4,766,118  8/1988  Combs ............................. 514/224.2

FOREIGN PATENT DOCUMENTS 272914   6/1988  European Pat. Off. ............ 544/105
1425430  2/1976  United Kingdom .

OTHER PUBLICATIONS

Bonte, et al, Eur. J. Med. Chem., 9, pp. 497–500 (1974).
Moussavi et al., Eur. J. Med. Chem., 24, pp. 55–60 (1989).
McEvoy et al., J. Org. Chem., 38, No. 23, pp. 4044–4048 (1973).
Combs et al., J. Med. Chem., 33, pp. 380–386 (1990).
Sastry et al., Chemical Abstracts vol. 112, No. 198278u (1989).

Primary Examiner—Cecilia Tsang
Assistant Examiner—Philip I. Datlow
Attorney, Agent, or Firm—Joseph J. Brindisi

[57] ABSTRACT

The invention relates to a process for the synthesis of compounds of the formula I

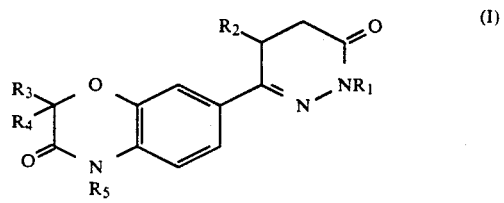

wherein $R_1$-$R_5$ are as defined herein.

The process is a multistep process which comprises acylating a 2-benzoxazolinone with an alkanoic anhydride to form an acylated carbamate, hydrolyzing the carbamate, reacting the resultant aminophenol with haloalkanoyl halide to form a substituted benzoxazine, reacting the benzoxazine with an aldehyde, alkylating the resultant aminomethyl compound with an alkylating agent to form a quaternary ammonium salt, reacting the salt with an alkali metal cyanide to form a nitrile, hydrolyzing the nitrile and reacting the resultant carboxylic acid with hydrazine.

The compounds are useful as cardiotonic and vasodilating agents and as inhibitors of phosphodiesterase fraction III and platelet aggregation. In addition, the compounds are active as smooth muscle relaxants and bronchodilators.

43 Claims, No Drawings

PROCESS FOR THE PREPARATION OF 6-(3,4-DIHYDRO-3-OXO-1,4(2H)-BENZOXAZIN-7-YL)-2,3,4,5-TETRAHYDROPYRIDAZIN-3-ONES

FIELD OF THE INVENTION

The invention relates to a process for the synthesis of compounds of the formula I

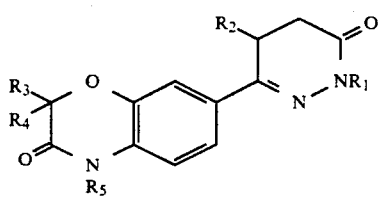

as further defined herein. The compounds are useful as cardiotonic and vasodilating agents and as inhibitors of phosphodiesterase fraction III and platelet aggregation. In addition, the compounds are active as smooth muscle relaxants and bronchodilators.

BACKGROUND OF THE INVENTION

U.S. Pat. Nos. 4,766,118 and 4,721,784 relate to benzoxazinyl-pyridazinone compounds, their uses and methods for making the compounds. Each of these patents discloses two reaction schemes for making 6-(3,4-dihydro-3-oxo-1,4(2H)-benzoxazin-7-yl)-2,3,4,5-tetrahydropyridazin-3-ones.

In one scheme, the initial starting material is a 5-alkanoyl-2-aminophenol. The use of that starting material, which has the alkanoyl group at the 5-position, is required since the group is converted to the tetrahydropyridazin-3-one moiety in the final product and since the carbonyl carbon of the alkanoyl group becomes the carbon that is bonded to the 7-position of the benzoxazine moiety in the final product. This scheme, however, does not teach a method for preparing a 5-alkanoyl-2-aminophenol from a 2-aminophenol precursor. The use of such a precursor as the starting material would be advantageous over the use of the disclosed starting material since it would be less costly to prepare the final product from a simpler (i.e., less functionalized) starting material.

In the other scheme, the formation of the tetrahydropyridazin-3-one moiety's bond to the 7-position of the benzoxazine moiety is effected by acylating a benzoxazine intermediate. That intermediate, however, must be substituted at its 6-position since the acylation only takes place at the 6-position if the 6-position of the benzoxazine is unsubstituted. Consequently this scheme provides no means for synthesizing a compound having a tetrahydropyridazin-3-one moiety linked to the 7-position of a benzoxazine moiety without the latter moiety also being substituted at its 6-position. In addition, this scheme only discloses that the reaction for introducing the alkanoyl (acyl) group, which is ultimately converted to the pyridazinone moiety in the final product, takes place at a later step in the reaction scheme (i.e., after the formation of the benzoxazine intermediate).

SUMMARY OF THE INVENTION

The present invention is directed to a novel method for synthesizing 6-(3,4-dihydro-3-oxo-1,4(2H)-benzoxazin-7-yl)-2,3,4,5-tetrahydropyridazin-3-ones of the general formula I:

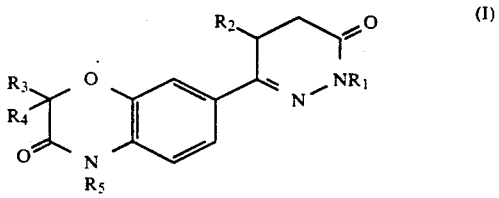

wherein
$R_1$ is selected from the group consisting of H, $C_{1-6}$ straight-chain or branched-chain alkyl, $C_{3-6}$ cycloalkyl and $C_{3-6}$ alkenyl; and
$R_2$, $R_3$, $R_4$ and $R_5$ each is selected from the group consisting of H, $C_{1-6}$ straight-chain or branched-chain alkyl and $C_{3-6}$ cycloalkyl, and
provided that where $R_1$ is other than H, the 2-nitrogen of the pyridazinone moiety is bonded to a carbon in $R_1$ other than an unsaturated carbon.

DETAILED DESCRIPTION OF THE INVENTION

The invention in its broadest aspects relates to the preparation of pyridazinone compounds which exhibit cardiotonic activity, vasodilating activity, platelet aggregating inhibitory activity and phosphodiesterase fraction III inhibitory activity. The benzoxazinyl-pyridazinone compounds demonstrating these activities are shown by the compound of formula I above, wherein C-6 of the pyridazinone moiety is attached at the C-7 of the benzoxazine moiety.

The preferred compounds made by the present invention are those wherein $R_1$ and $R_5$ are hydrogen, $R_2$, $R_3$ and $R_4$ are each independently H or $CH_3$.

The $C_{1-6}$ straight-chain or branched-chain alkyl moiety includes such groups as methyl, ethyl, isopropyl or tert-butyl; the $C_{3-6}$ cycloalkyl moiety includes such groups as cyclopropyl, cyclohexyl or methylcyclopentyl; and the $C_{3-6}$ alkenyl moiety includes such groups as propenyl, methylpropenyl or butenyl.

The process for preparing the compounds is shown in scheme I.

SCHEME I

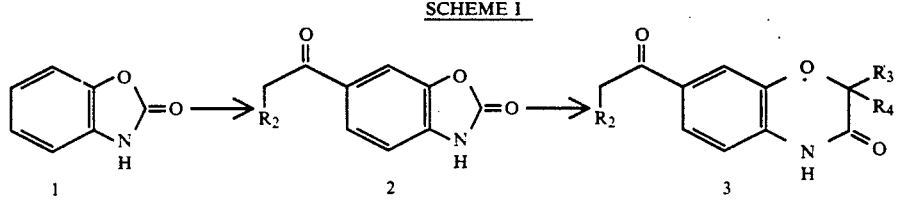

SCHEME I

-continued

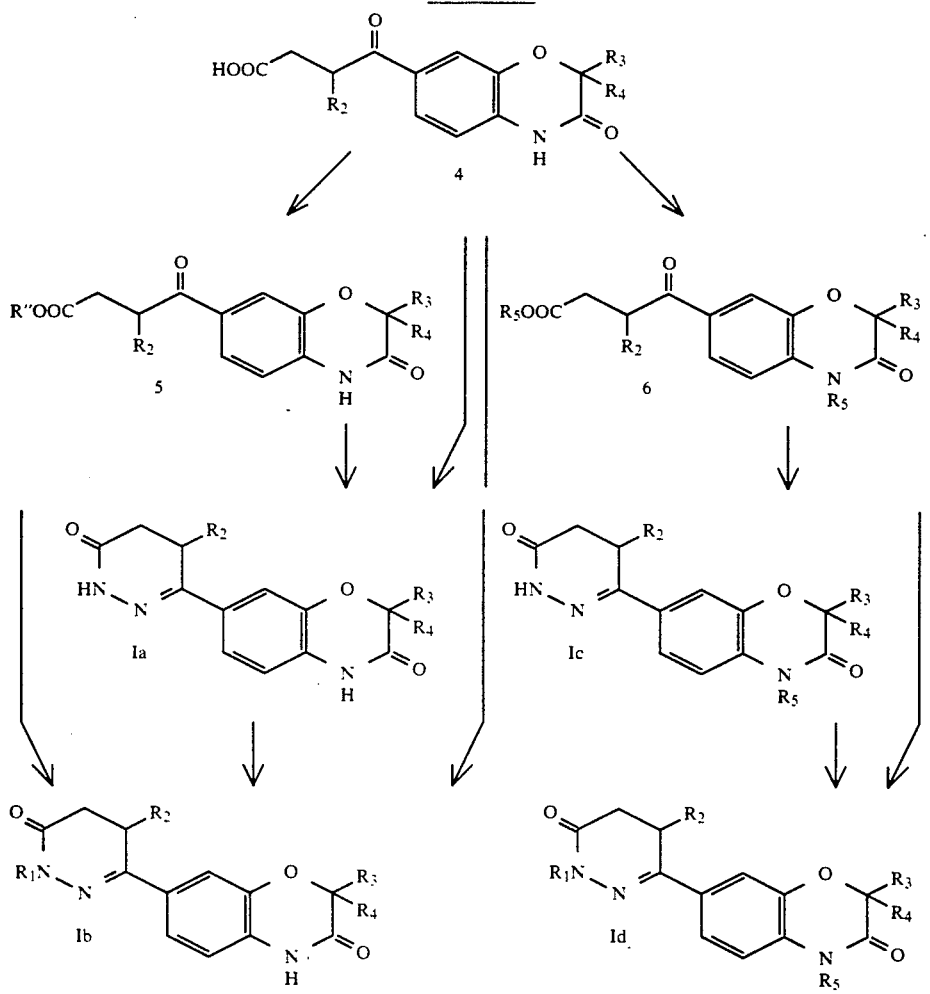

in the first step of Scheme I, 2-benzoxazolinone 1 (a carbamate), is acylated with an alkanoic anhydride of the formula $(R_2CH_2CO)_2O$, wherein $R_2$ is as defined above (e.g., propionic anhydride or acetic anhydride), to form an acylated carbamate 2. The method of Bonte et al. (*Eur. J. Med. Chem.*, 9, 491 (1974)) is employed in this reaction except that Eaton's reagent (*J. Org. Chem.*, 38, 4071 (1973)) is used instead of polyphosphoric acid. The method is essentially described in British Patent 1,425,430.

In particular, the Eaton's reagent is prepared by heating a mixture of phosphorous pentoxide and a lower ($C_{1-6}$) alkanesulfonic acid (e.g., methanesulfonic acid) from about 50° C. to about 70° C. until all the solid dissolves. To this reagent solution is added the 2-benzoxazolinone, and the resultant mixture is stirred for about 30 minutes before it is cooled to about 22° C. To this cold solution is added the alkanoic anhydride of the formula $(R_2CH_2CO)_2O$ (e g , acetic or propionic anhydride), and this resultant mixture is stirred at about 22° C. for about 20 hours to about 30 hours. The mixture is then quenched by pouring it into cold water whereupon the temperature is allowed to rise to between about 50° C. to about 60° C. During this quenching, ice is added to keep the temperature around that range. The temperature of the quenched mixture is then allowed to drop to about 40° C. before the mixture is cooled to about 15° C. thereby effecting the precipitation of the product.

Without isolating 2, it is then reacted by applying the general two-step method of Moussavi et al., (*Eur. J. Med. Chem..* 14. 55 (1989) to give a 7-alkanoyl-3,4-dihydro-3-oxo-1,4(2H)-benzoxazine 3.

In the first step of a two-step method, the carbamate (—N—C(O)—O—) moiety in compound 2 is hydrolyzed under basic conditions to yield the corresponding acylated aminophenol. The removal of the carbonyl takes place in water to which a base such as an alkali carbonate (e.g., $Na_2CO_3$ or $K_2CO_3$), an alkali hydroxide (e.g., NaOH or KOH) or an alkaline earth hydroxide (e.g., $Mg(OH)_2$ or $Ca(OH)_2$) is added. The hydrolyis is effected by heating the solution to about reflux for about 6 hours to about 30 hours.

The second step of the two-step method which involves both an alkylation reaction and an acylation reaction of the resultant aminophenol, is also described by Shridhar et al. (*Org. Prep. Int.*, 14, 195 (1982)) and in U.S. Pat. No. 4,358,455 to J. G. Atkinson et al. The reaction is carried out in an aqueous solvent, an organic solvent, or a mixed solvent (i.e., aqueous-organic solvent) wherein the organic solvent is a ketone (e.g., acetone or methyl isobutyl ketone). This reaction mixture is also basified by using a base such as an alkali alkoxide (e.g., sodium ethoxide or potassium tert-butoxide), an alkali carbonate, an alkali hydroxide or an alkaline earth hydroxide.

In particular, the basified solution containing the acylated aminophenol is cooled to about 0° C. and a 2-haloalkanoyl halide of the formula $XR_3R_4CCOX$, wherein $R_3$ and $R_4$ are as defined above and X is the same or different species selected from the group consisting of chloro, bromo and iodo, is added slowly thereto. Following the addition of the 2-haloalkanoyl halide, the mixture is heated to about reflux for about 9 hours to about 16 hours to yield compound 3. The preferred reaction solvent mixture is a water-methyl isobutyl ketone solution and the preferred haloalkanoyl halides are 2-chloroacetyl chloride, 2-chloropropionyl chloride or 2-chloro-2-methylpropionyl chloride.

Compound 3 is then converted to compound 4 employing the three-step method of McEvoy and Allen (*J. Org. Chem.*, 38, 4044 (1973)).

Compound 3 is reacted in a Mannich reaction with a secondary amine or preferably with its hydrohalide (e.g. HCl) or acetate salt and an aldehyde (e.g., formaldehyde or paraformaldehyde) to yield the corresponding substituted aminomethyl compound. The secondary amine is of the formula $HN(R')_2$ wherein R' is the same or different group and is a lower ($C_{1-6}$) alkyl, lower ($C_{1-6}$) hydroxyalkyl, lower ) alkenyl, phenyl lower alkyl and lower ) cycloalkyl lower alkyl. The secondary amine also includes cyclic secondary amines formed by the covalent bonding of the R's together with the nitrogen. Examples of the secondary amines include diethylamine, morpholine, dimethylamine, tetrahydroisoquinoline, diethanolamine, diallylamine, dibenzylamine, piperidine and isopropylmethylamine. This reaction takes place in water or in an organic solvent such as cycloethers (e.g., tetrahydrofuran or dioxane), $C_{1-4}$ alcohols (e.g., methanol or ethanol) and alkanoic acid anhydrides (e.g., acetic or propionic anhydride). The reaction mixture is heated to about reflux for about 2 hours to about 4 hours. This reaction is preferentially carried out using dimethylamine hydrochloride and formaldehyde in acetic anhydride.

The product from the Mannich reaction is then reacted with an alkylating reagent of the formula RL wherein L is a displaceable group to yield the corresponding quaternary ammonium compound. R is $C_{1-6}$ straight-chain or branched alkyl and $C_{3-6}$ cycloalkyl; L is halo (e.g., chloro, bromo or iodo), —OS(O)Cl or —$OSO_3R$ wherein R is as defined above. Examples of RL include methyl iodide, 2-chloropropane, diethyl sulfate, dimethyl sulfate, methyl chlorosulfite, and propyl chlorosulfite. Suitable solvents for this reation include water or organic solvents such as $C_{1-4}$ alcohols (e.g., methanol or ethanol) and ketones (e.g., acetone or 2-butanone). The reaction is effected from about 10° C. to about the reflux temperature. The reaction takes about 3 days to about 5 days at lower temperatures whereas it takes about 3 hours to about 8 hours at higher temperatures. It is preferably effected by heating the mixture to about reflux for about 5 hours to about 8 hours.

That quaternary ammonium salt is then converted to the corresponding nitrile by treating the salt with an alkali metal cyanide such as potassium or sodium cyanide. This reaction takes place in an aqueous solution, an aqueous alcoholic solution, an anhydrous alcoholic solution or an inert solvent (e.g., dimethylformamide or dimethylsulfoxide) wherein the alcohols are $C_{1-4}$ alcohols (e.g., methanol or ethanol). The reaction is effected at about 22° C. to the reflux temperature for about 20 hours to about 30 hours. It is preferably effected by reacting the mixture at about 22° C. for about 22 hours to about 30 hours.

Finally, that nitrile is subjected to acid hydrolysis to yield the corresponding acid compound 4. This reaction takes place under acidic conditions in water wherein a mineral acid such as hydrochloric acid or sulfuric acid is employed. In particular, the normality of the hydrolysis solution is adjusted from about 5.0N to about 8.0N and the mixture is heated to about reflux for about 0.5 hours to about 2.5 hours.

The compounds of formulae Ia or Ib are then prepared by heating a solution of 4 to about reflux temperature for about 1 hour to about 8 hours with a hydrazine derivative of the formula $R_1 HN-NH_2$, wherein $R_1$ is as defined above and where the hydrazine nitrogen is bonded to a carbon in $R_1$ other than an unsaturated carbon.

It is preferred to use at least an equivalent amount of the aforesaid hydrazine to the amount of 4. This reaction is carried out in an aqueous or an alcohol solution, wherein an alcohol such as methanol, ethanol or isopropanol is employed.

Compounds of formulae Ia or Ib are prepared alternatively by first esterifying compound 4 and then treating the corresponding ester 5 with the aforesaid hydrazine as noted above.

The esterification is accomplished under acidic reaction conditions by suspending 4 in a $C_{1-3}$ alcohol (e.g., R"OH, wherein R" is a $C_{1-3}$ alkyl) such as methanol or ethanol and then adding thereto an alkanoyl halide such as acetyl chloride. The reaction is effected at about room temperature in about 1 day to about 3 days or at about reflux temperature in about 0.5 hour to about 4 hours.

Alternatively, compound 4 is esterified under acidic reaction conditions by adding an acid such as hydrochloric, sulfuric or p-toluenesulfonic acid to a $C_{1-3}$ alcohol, R"OH, (e.g., methanol or ethanol) containing compound 4. The acid is used in about 5 to about 10 weight % to 4. Alternatively, a strong acid ion exchange resin is used in place of the aforesaid acid, and the resin is used in about 10 to about 30 weight % to 4. The reaction itself is effected at about reflux temperature in about 1.5 hours to about 4 hours.

In order to shift the equilibrium in favor of the formation of 5 under acidic conditions, the water that is formed during the esterification process is removed by adding to the esterification reaction mixture another organic liquid such as benzene or toluene to form an azeotrope; from which water is removed during reflux in an apparatus such as a Dean Stark trap or a Soxhlet extractor containing a drying agent (e.g., molecular sieves).

Compound 4 is also esterified to prepare 5 by treating 4 with an alkali or an alkaline earth base as described above to form the alkali or alkaline earth salt of 4, and then treating the salt with an alkylating agent of the formula R"L wherein R" is $C_{1-3}$ alkyl; L is halo (e.g., chloro, bromo or iodo), —OS(O)Cl or —$OSO_3R$" wherein R" is as defined above. The alkylation takes place in an organic solvent such as a ketone (e.g., acetone), a lower alcohol (e.g., methanol or isopropanol), xylene, benzene dimethylformamide or dimethylsulfoxide, at about 0° C. to about reflux temperature from about 0.5 hour to about 24 hours.

The compounds of formula Ib are alternatively prepared by alkylating Ia under an inert atmosphere or dry conditions (e.g., nitrogen atmosphere) at the 2-position of the pyridazinone moiety. This alkylation is carried out by treating compounds of formula Ia with an alkali metal base such as sodium hydride in an inert solvent, e.g., dimethylformamide or dimethyl sulfoxide) to yield the corresponding salt of Ia and then adding to the resultant salt an alkylating agent of the formula $R_1 L_1$ wherein $R_1$ is as defined above except for H (i.e., $C_{1-6}$ straight-chain or branched alkyl, $C_{3-6}$ cycloalkyl and $C_{3-6}$ alkenyl); $L_1$ is halo (e.g., chloro, bromo or iodo), $-OS(O)Cl$ or $-OSO_3R_1$ wherein $R_1$ is as defined above except for H and $L_1$ is bonded to a carbon in $R_1$ other than an unsaturated carbon. The reaction occurs at about 0° C. to about reflux temperature for about 0.5 hour to about 24 hours to give the N-alkylated compounds of the formula Ib.

Alternatively, the compound of the formula I which is alkylated at the 2-position of the pyridazinone moiety is formed by reacting a hydrazine derivative of the formula $R_1 HN-NH_2$, wherein $R_1$ is as defined above except for H and where the hydrazine nitrogen is bonded to a carbon in $R_1$ other than an unsaturated carbon, with compound 4 under the same reaction conditions as when 4 is reacted with hydrazine.

The preparation of compounds of formulae Ic or Id, which are alkylated at the 4-position of the benzoxazinyl moiety, was carried out by treating compound 4 under an inert atmosphere or under dry conditions with about two equivalents of an alkali metal base such as sodium hydride in an inert solvent (e.g., dimethylformamide or dimethyl sulfoxide) and then adding to the resultant salt an alkylating agent of the formula $R_5 L_2$ to the solvent wherein $R_5$ is as defined above except for H (i.e., $C_{1-6}$ straight-chain or branched alkyl and $C_{3-6}$ cycloalkyl); $L_2$ is halo (e.g., chloro, bromo or iodo), $-OS(O)Cl$ or $-OSO$ wherein $R_5$ is as defined above except for H. The reaction occurs at about 0° C. to about 40° C. for about 0.5 hour to about 8 hours to give the N-(alkylated) ester compound, 6, which then reacted with the aforesaid hydrazine derivative of the formula $R_1 HN-NH_2$, wherein $R_1$ is as defined above to produce compounds of formulae Ic or Id.

In addition, although the compounds of the formula I, i.e., where $R_2$ is other than H or where $R_3$ and $R_4$ are not the same group, are obtained as racemic mixtures, however, these mixtures are resolvable to enantiomers. Standard methods are applicable in resolving the mixtures, and, in particular, chiral (enantiomeric) HPLC methods are employed in effecting the enantiomeric separations.

The following examples describe the invention in greater particularity and are intended to be a way of illustrating but not limiting the invention.

EXAMPLES

Example 1: Preparation of 6-(3,4-Dihydro-3-oxo-1,4(2H)-benzoxazin-7-yl)-2,3,4,5-tetrahydro-5-methylpryidazin-3-one

Step a: 6-Propionyl-2-benzoxazolinone

Phosphorous pentoxide (300 g, 2.10 moles) was added to methanesulfonic acid (3000 g) in a 5-liter three-neck round bottom flask fitted with an overhead mechanical stirrer, thermometer and 500 ml addition funnel. The mixture was heated to 50° C. for one hour or until all of the solid was dissolved. While still at 50° C. 2-benzoxazolinone (270 g, 2.0 moles) was added in one portion and the blue mixture stirred for 30 minutes before cooling to room temperature in an ice-water bath. Propionic anhydride (136 ml, 1.0 moles) was added dropwise to the solution over 20 minutes. After stirring at room temperature for 24 hours, the mixture was poured into 5 liters of cold water and the temperature allowed to climb to about 60° C. Ice was added to keep the temperature between 50° C. and 60° C. during the quenching. The temperature was allowed to drop to 40° C. before the mixture was cooled in an ice bath to 15° C. and the precipitate collected by suction filtration. The filter cake was washed with water then with a minimum amount of cold methanol, and dried to yield 152 g, 40%. mp 203-204.

Step b: 3,4-Dihydro-7-(1-oxopropyl)-3-oxo-1,4(2H)-benzoxazine

6-Propionyl-2-benzoxazolinone (147 g, 0.77 moles) was placed in a 5-liter three-neck round bottom flask with an overhead mechanical stirrer and a reflux condenser. Aqueous 10% sodium carbonate solution (1.5 liters) was added and the mixture heated at reflux for 24 hours.

Sodium bicarbonate (84 g, 1.0 mole) was added to the cooled reaction mixture followed by methyl isobutyl ketone (900 ml). Chloroacetyl chloride (75 ml, 0.94 moles) was added slowly to the vigorously stirred two phase system. When addition was complete the ice bath was replaced with a heating mantle and the reaction heated at reflux for 12 hours. Upon cooling in ice, crystals of the product formed and were collected by filtration and washed with water followed by a minimum amount of diethyl ether (yield 75 g, 50%). A second crop was obtained by separation of the two layers of the filtrate and extracting the water layer with ethyl acetate. The combined organic layers were evaporated to dryness and the residue triturated with diethyl ether. The product was collected by filtration and washed with ether to give an additional 30 g of product. Total yield 70%, mp 170°-172° C.

The following compounds were made by the above procedure, using the appropriate starting materials: 3,4-dihydro-2-methyl-7-(1-oxopropyl)-3-oxo-1,4(2H)-benzoxazine, mp 179°-179.5° C.; and 3,4-dihydro-2,2-dimethyl-7-(1-oxopropyl)-3-oxo-1,4(2H)-benzoxazine, mp 153°-155° C.

Step c: 3,4-Dihydro-7-(3-dimethylamino-2-methyl-1-oxopropyl-3-oxo-1,4(2H)-benzoxazine 3,4-Dihydro-7-(1-oxopropyl)-3-oxo-1,4(2H)-benzoxazine (75 g) was added to a mixture of 37% formalin (36 ml, dimethylamine hydrochloride (44 g) and acetic anhydride (118 ml) which had been heated to give a homogeneous solution. The resultant mixture was heated at reflux for 2.5 hours, then cooled and acetone (100 ml) added. Volatiles were removed by evaporation and the residue taken up in 0.5N HCl (700 ml) and washed with ethyl acetate (2×250 ml). The aqueous layer was chilled in ice and 50% NaOH added until pH 10.5 was achieved. A white precipitate was collected and washed with water. Drying gave 76 g (75%) of a tan powder which was used in the next step without further purification.

Step d:
3,4-Dihydro-7-(3-dimethylamino-1-oxopropyl)-3-oxo-1,4(2H)-benzoxazine methiodide 3,4-Dihydro-7-(2-methyl-3-dimethylamino-1-oxopropyl)-3-oxo-1,4(2H)-benzoxazine (76 g) was dissolved in acetone (750 ml) and iodomethane (45 ml) was added. The mixture was heated at reflux with stirring for 3 hours and then cooled in ice. The crystals that formed were collected by filtration and washed with acetone. Drying gave 110 g (99%) of a light tan solid, mp 223°–224° C.

Step e:
4-(3,4-Dihydro-3-oxo-1,4(2H)-benzoxazin-7-yl)-4-oxo-3-methylbutyronitrile 3,4-Dihydro-7-(2-methyl-3-dimethylamino-1-oxopropyl)-3-oxo-1,4(2H)-benzoxazine methiodide (110 g) was dissolved in methanol (400 ml) and water (1000 ml). Potassium cyanide (80 g) dissolved in water (200 ml) was added and the mixture stirred at room temperature for 24 hours. The white precipitate was collected by filtration and washed with water to give 65.7 g (99%) of the titled nitrile, mp 183°–184° C.

Step f:
4-(3,4-Dihydro-3-oxo-1,4(2H)-benzoxazin-7-yl)-4-oxo-3-methylbutyric acid 4-(3,4-Dihydro-3-oxo-1,4(2H)-benzoxazin-7-yl)-4-oxo-3-methylbutyronitrile (65 g) was heated at reflux for 1.5 hours in 6N HCl (600 ml). The solution was poured into ice water (600 ml) and the resulting solid was collected by filtration, washed with water and recrystallized from acetic acid. After washing with ethanol and then with ethyl ether the product was dried to give 31.6 g of pure white 4-(3,4-dihydro-3-oxo-1,4(2H)-benzoxazin-7-yl)-4-oxo-3-methylbutyric acid, mp 170°–172° C.

The following compounds were made by the above procedures (steps 1(a–f)), using the appropriate starting materials:
4-(3,4-dihydro-2-methyl-3-oxo-1,4(2H)-benzoxazin-7-yl)-4-oxo-3-methylbutyric acid, mp 186°–188° C.; and
4-(3,4-dihydro-2,2-dimethyl-3-oxo-1,4(2H)-benzoxazin-7-yl)-4-oxo-3-methylbutyric acid, mp 174°–175.5° C.

Step g: Methyl 4-(3,4-dihydro-3-oxo-1,4(2H)-benzoxazin-7-yl)-4-oxo-3-methylbutyrate 4-(3,4-Dihydro-3-oxo-1,4(2H)-benzoxazin-7-yl)-4-Oxo-3-methylbutyric acid (5 g) was suspended in methanol (50 ml) and acetyl chloride (0.5 ml) added. The mixture was heated on a steam bath until all of the solid dissolved. The solvent was evaporated at reduced pressure providing the ester as a white foam which was recrystallized from ethyl acetate-methanol to give the product as white crystals, yield 5 g, mp 95°–98° C.

$C_{14}H_{15}NO_5$, Theor.: C, 60.63; H, 5.46; N, 5.05. Found: C, 60.72; H, 5.52; N, 5.17.

Step h:
6-(3,4-Dihydro-3-oxo-1,4(2H)-benzoxazin-7-yl)-2,3,4,5-tetrahydro-5-methylpyridazin-3-one 4-(3,4-Dihydro-3-oxo-1,4(2H)-benzoxazin-7-yl)-4-oxo-3-methylbutyric acid (31 g, 0.12 moles) was dissolved in ethanol (300 ml) and anhydrous hydrazine (4.7 ml, 0.15 moles) was added. The mixture was heated at reflux overnight. White crystals formed after the mixture was cooled. The crystals were collected by filtration and washed well with ethanol. The solid was dried under vacuum giving 28.5 g (93%) of the titled compound, mp 299°–302° C.

The following compounds were made by the above procedure, using the appropriate starting materials (e.g., of steps 1(f) or 1(g)):
6-(3,4-dihydro-2-methyl-3-oxo-1,4(2H)-benzoxazin-7-yl)-2,3,4,5-tetrahydro-5-methylpyridazin-3-one, mp 269°–270° C.; and 6-(3,4-dihydro-2,2-dimethyl-3-oxo-1,4(2H)-benzoxazin-7-yl)-2,3,4,5-tetrahydro-5-methylpyridazin-3-one, mp 289.5°–290° C.

Example 2: Preparation of 6-(3,4-dihydro-4-methyl-3-oxo-1,4(2H)-benzoxazin-7-yl)-2,3,4,5-tetrahydro-5-methylpryidazin-3-one

Step a: Methyl 4-(3,4-dihydro-4-methyl-3-oxo-1,4(2H)-benzoxazin-7-yl)-4-oxo-3-methylbutyrate 4-(3,4-Dihydro-3-oxo-1,4(2H)-benzoxazin-7-yl)-4-oxo-3-methylbutyric acid (3.3g) was dissolved in dimethylformamide. Two equivalents of 60% sodium hydride in an oil suspension (0.489 moles) were added. After 0.5 hour, two equivalents of methyliodide were added. The mixture was allowed to stir under nitrogen for 12 hours, and then poured into water. The product was collected by filtration, or by extraction into ethyl acetate and the subsequent evaporation of the extraction solvent. The resultant brown oil (66%) was used in the next step without further purification.

The following compounds were made by the above procedure, using the appropriate starting materials:
methyl 4-(3,4-dihydro-2,4-dimethyl-3-oxo-1,4(2H)-benzoxazin-7-yl)-4-oxo-3-methylbutyrate (oil); and methyl 4-(3,4-dihydro-2,2,4-trimethyl-3-oxo-1,4(2H)-benzoxazin-7-yl)-4-oxo-3-methylbutyrate (oil).

Step b: 6-(3,4-Dihydro-4-methyl-3-oxo-1,4(2H)-benzoxazin-7-yl)-2,3,4,5-tetrahydro-5-methylpyridazin-3-one Methyl 4-(3,4-dihydro-4-methyl-3-oxo-1,4(2H)-benzoxazin-7-yl)-4-oxo-3-methylbutyrate was treated with hydrazine as in example 1 to give the title compound, mp 188°–190° C.

The following compounds were made by the above procedure, using the appropriate starting materials:
6-(3,4-dihydro-2,4-dimethyl-3-oxo-1,4(2H)-benzoxazin-7-yl)-2,3,4,5-tetrahydro-5-methylpyridazin-3-one, partial melting 222°–224° C. and then from 240°–242° C.; and
6-(3,4-dihydro-2,2,4-trimethyl-3-oxo-1,4(2H)-benzoxazin-7-yl)-2,3,4,5-tetrahydro-5-methylpyridazin-3-one, mp 240°–242° C.

Example 3: Preparation of 6-(3,4-dihydro-3-oxo-1,4(2H)-benzoxazin-7-yl)-2,5-dimethyl-2,3,4,5-tetrahydropyridazin-3-one

Step a:
6-(3,4-dihydro-3-oxo-1,4(2H)-benzoxazin-7-yl)-2,5-dimethyl-2,3,4,5-tetrahydropyridazin-3-one 4-(3,4-Dihydro-3-oxo-1,4(2H)-benzoxazin-7-yl)-4-oxo-3-methylbutyric acid (1.56 g, 6.0 mmoles) was dissolved in ethanol (300 ml) and methylhydrazine (0.33 ml, 6.0 mmoles) was added. The mixture was heated at reflux for 2 hours, and then cooled to yield to yield the titled compound. The crystals were collected by filtration, recrystallized from ethanol, and recollected by filtration. The solid was dried under vacuum to yield 1.0 g of the titled compound, mp 204°–206° C.

$C_{14}H_{15}N_3O_3$, Theor.: C, 61.53; H, 5.53; N, 15.38. Found: C, 61.32; H, 5.55; N, 15.68.

Example 4: Preparation of 6-(3,4-dihydro-4-methyl-3-oxo-1,4(2H)-benzoxazin-7yl)-2,5-dimethyl-2,3,4,5-tetrahydropyridazin-3-one Step a: 6-(3,9-Dihydro-4-methyl-3-oxo-1,4(2H)-benzoxazin-7-yl)-2,5-dimethyl-2,3,4,5-tetrahydropyridazin-3-one 6-(3,4-dihydro-4-methyl-3-oxo-1,4(2H)-benzoxazin-7-yl)-2,3,4,5-tetrahydro-5-methylpyridazin-3-one (3 g) is suspended in 50 ml of dimethylformamide and one equivalent of 60% sodium hydride in oil is added. When gas evolution ceases, one equivalent of methyl iodide is added and the mixture is allowed to stand for 1.5 hours and then for one hour at 40° C. The mixture is cooled and then poured into 200 ml of ice water, to yield a precipitate that is collected by filtration, washed with water and recrystallized from ethanol. The material is further purified by chromatography on silica gel.

The following compounds are produced as a mixture and separated by chromatography by the above procedure, using the appropriate starting material:
6-(3,4-dihydro-3-oxo-1,4(2H)-benzoxazin-7-yl)-2,5-dimethyl-2,3,4,5-tetrahydropyridazin-3-one, mp 204°–206° C.;
and 6-(3,4-dihydro-4-methyl-3-oxo-1,4(2H)-benzoxazin-7-yl)-2,5-dimethyl-2,3,4,5-tetrahydropyridazin-3-one, mp 188°–190° C.

We claim:

1. A process for preparing a compound of the formula

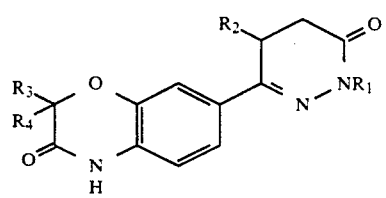

wherein
$R_1$ is selected from the group consisting of H, $C_{1-6}$ straight-chain alkyl, $C_{1-6}$ branched-chain alkyl, $C_{3-6}$ cycloalkyl and $C_{3-6}$ alkenyl; and
$R_2$, $R_3$ and $R_4$ each is selected from the group consisting of H, $C_{1-6}$ straight-chain alkyl, $C_{1-6}$ branched-chain alkyl and $C_{3-6}$ cycloalkyl,
provided that where $R_1$ is other than H, the 2-nitrogen of the pyridazinone moiety is bonded to a carbon in $R_1$ other than an unsaturated carbon,
which comprises the steps of:
(a) acylating 2-benzoxazolinone with an alkanoic anhydride of the formula $(R_2CH_2CO)_2O$, wherein $R_2$ is as defined above, in the presence of Eaton's reagent to yield an acylated carbamate compound of the formula

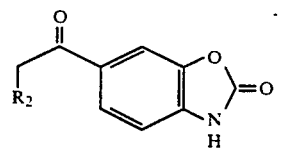

(b) hydrolyzing the resultant acylated carbamate under basic conditions to yield an aminophenol compound of the formula

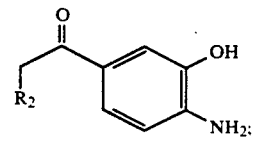

(c) reacting the resultant aminophenol compound with a 2-haloalkanoyl halide of the formula $XR_3R_4CCOX$, wherein $R_3$ and $R_4$ are as defined above and X is selected from the group consisting of chloro, bromo and iodo to yield a benzoxazine compound of the formula

(d) reacting the resultant benzoxazine compound with an aldehyde selected from the group consisting of formaldehyde and paraformaldehyde and a secondary amine of the formula $HN(R')_2$ wherein R' is the same or different group selected from the group consisting of lower alkyl, lower hydroxyalkyl, lower alkenyl, phenyl lower alkyl and lower cycloalkyl lower alkyl, and where the covalent bonding of the R's together with the nitrogen form a cyclic secondary amine, to yield a substituted aminomethyl compound of the formula

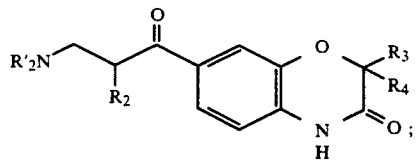

(e) alkylating the resultant substituted aminomethyl compound with an alkylating agent of the formula RL wherein R is $C_{1-6}$ straight-chain or branched alkyl and $C_{3-6}$ cycloalkyl, and L is selected from the group consisting of halo, —OS(O)Cl and —O-SO$_3$R wherein R is as defined above, to yield a quarternary ammonium compound of the formula

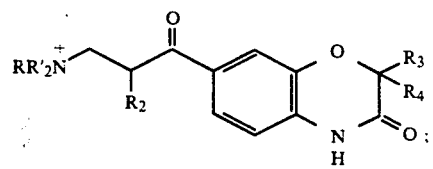

(f) reacting the resultant quaternary ammonium compound with an alkali metal cyanide to yield a nitrile compound of the formula

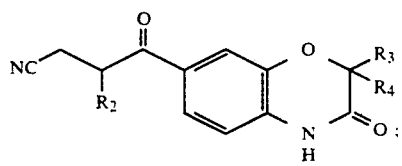

(g) hydrolyzing under acidic conditions the resultant nitrile compound to yield a carboxylic acid compound of the formula

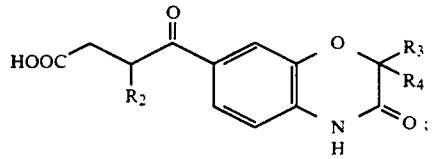

and (h) reacting the resultant carboxylic acid compound with a hydrazine derivative of the formula $R_1$HN—$NH_2$, wherein $R_1$ is as defined above and provided where $R_1$ is other than H, the hydrazine nitrogen is bonded to a carbon in $R_1$ other than an unsaturated carbon.

2. The process of claim 1 wherein said alkanoic anhydride is selected from the group consisting of acetic anhydride and propionic anhydride.

3. The process of claim 1 wherein said 2-haloalkanoyl halide is selected from the group consisting of chloroacetyl chloride, 2-chloropropionyl chloride and 2-chloro-2-methylpropionyl chloride.

4. The process of claim 1 wherein said secondary amine is selected from the group consisting of diethylamine, morpholine, dimethylamine, tetrahydroisoquinoline, diethanolamine, diallylamine, dibenzylamine, piperidine and isopropylmethylamine.

5. The process of claim 4 wherein said secondary amine is dimethylamine.

6. The process of claim 1 wherein said alkylating agent of step (e) is methyl iodide.

7. The process of claim 1 wherein said alkali metal cyanide is potassium cyanide.

8. A process for preparing a compound of the formula

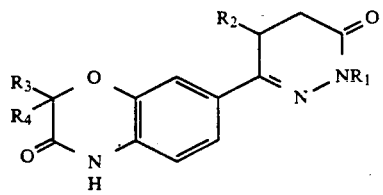

wherein $R_1$ is $C_{1-6}$ straight-chain alkyl, $C_{1-6}$ branched-chain alkyl, $C_{3-6}$ cycloalkyl or $C_{3-6}$ alkenyl; and $R_2$, $R_3$ and $R_4$ each is selected from the group consisting of H, $C_{1-6}$ straight-chain alkyl, $C_{1-6}$ branched-chain alkyl and $C_{3-6}$ cycloalkyl, provided that the 2-nitrogen of the pyridazinone moiety is bonded to a carbon in $R_1$ other than an unsaturated carbon, which comprises the steps of:

(a) acylating 2-benzoxazolinone with an alkanoic anhydride of the formula $(R_2CH_2CO)_2$ wherein $R_2$ is as defined above, in the presence of Eaton's reagent to yield an acylated carbamate compound of the formula

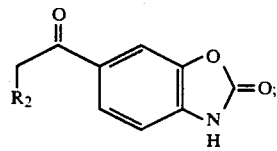

(b) hydrolyzing the resultant acylated carbamate under basic conditions to yield an aminophenol compound of the formula

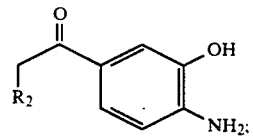

(c) reacting the resultant aminophenol compound with a 2-haloalkanoyl halide of the formula $XR_3R_4CCOX$, wherein $R_3$ and $R_4$ are as defined above and X is selected from the group consisting of chloro, bromo and iodo to yield a benzoxazine compound of the formula

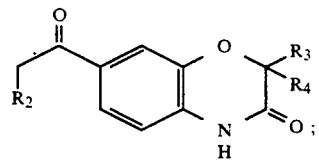

(d) reacting the resultant benzoxazine compound with an aldehyde selected from the group consisting of formaldehyde and paraformaldehyde and a secondary amine of the formula $HN(R')_2$ wherein R' is the same or different group selected from the group consisting of lower alkyl, lower hydroxyalkyl, lower alkenyl, phenyl lower alkyl and lower cycloalkyl lower alkyl, and where the covalent bonding of the R's together with the nitrogen form a cyclic secondary amine, to yield a substituted aminomethyl compound of the formula

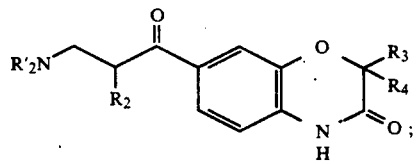

(e) alkylating the resultant substituted aminomethyl compound with an alkylating agent of the formula RL wherein R is $C_{1-6}$ straight-chain or branched alkyl and $C_{3-6}$ cycloalkyl, and L is selected from the group consisting of halo, —OS(O)Cl and —O-

SO$_3$R wherein R is as defined above, to yield a quarternary ammonium compound of the formula

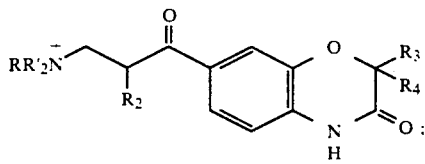

(f) reacting the resultant quaternary ammonium compound with an alkali metal cyanide to yield a nitrile compound of the formula

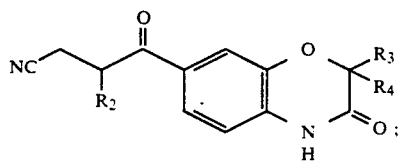

(g) hydrolyzing under acidic conditions the resultant nitrile compound to yield a carboxylic acid compound of the formula

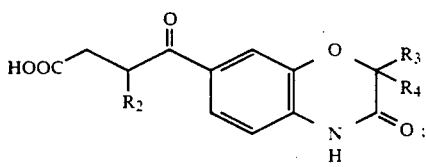

(h) reacting the resultant carboxylic acid compound with hydrazine to yield a 6-(3,4-dihydro-3-oxo-(2H)-1,4-benzoxazin-7-yl)-2,3,4,5-tetrahydropyridazin-3-one compound of the formula

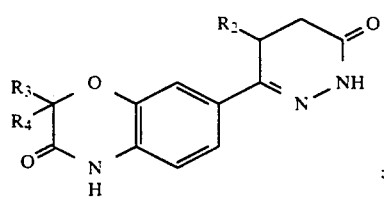

and (i) reacting the resultant 6-(3,4-dihydro-3-oxo-1,4(2H)-benzoxazin-7-yl)-2,3,4,5-tetrahydropyridazin-3-one compound with an alkali metal base in a solvent and then adding an alkylating agent of the formula R$_1$L$_1$ to the solvent wherein R$_1$ is as defined above except for H, L$_1$ is selected from the group consisting of halo, —OS(O)Cl and —O-SO$_3$R$_1$ wherein R$_1$ is as defined above except for H and L$_1$ is bonded to a carbon in R$_1$ other than an unsaturated carbon.

9. The process of claim 8 wherein said alkanoic anhydride is selected from the group consisting of acetic anhydride and propionic anhydride.

10. The process of claim 8 wherein said 2-haloalkanoyl halide is selected from the group consisting of chloroacetyl chloride, 2-chloropropionyl chloride and 2-chloro-2-methyl-propionyl chloride.

11. The process of claim 8 wherein said secondary amine is selected from the group consisting of diethylamine, morpholine, dimethylamine, tetrahydroisoquinoline, diethanolamine, diallylamine, dibenzylamine, piperidine and isopropylmethylamine.

12. The process of claim 11 wherein said secondary amine is dimethylamine.

13. The process of claim 8 wherein said alkylating agent of step (e) is methyl iodide.

14. The process of claim 8 wherein said alkali metal cyanide is potassium cyanide.

15. A process for preparing a compound of the formula

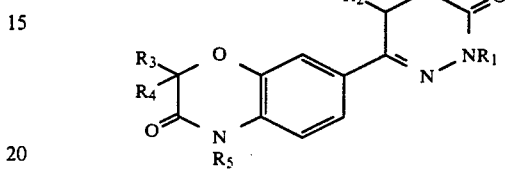

wherein

R$_1$ is selected from the group consisting of H, C$_{1-6}$ straight-chain alkyl, C$_{1-6}$ branched-chain alkyl, C$_{3-6}$ cycloalkyl and C$_{3-6}$ alkenyl;

R$_2$, R$_3$ and R$_4$ each is selected from the group consisting of H, C$_{1-6}$ straight-chain alkyl, C$_{1-6}$ branched-chain alkyl and C$_{3-6}$ cycloalkyl; and R$_5$ is selected from the group consisting of C$_{1-6}$ straight-chain alkyl, C$_{1-6}$ branched-chain alkyl and C$_{3-6}$ cycloalkyl, provided that where R$_1$ is other than H, the 2-nitrogen of the pyridazinone moiety is bonded to a carbon in R$_1$ other than an unsaturated carbon, which comprises the steps of:

(a) acylating 2-benzoxazolinone with an alkanoic anhydride of the formula (R$_2$CH$_2$CO)$_2$O, wherein R$_2$ is as defined above, in the presence of Eaton's reagent to yield an acylated carbamate compound of the formula

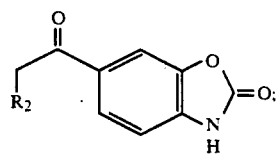

(b) hydrolyzing the resultant acylated carbamate and basic conditions to yield an aminophenol compound of the formula

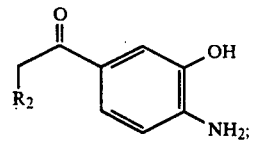

(c) reacting the resultant aminophenol compound with a 2-haloalkanoyl halide of the formula XR$_3$R$_4$CCOX, wherein R$_3$ and R$_4$ are as defined above and X is selected from the group consisting of chloro, bromo and iodo to yield a benzoxazine compound of the formula

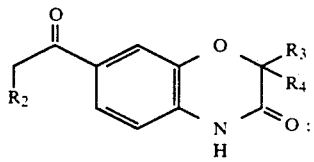

(d) reacting the resultant benzoxazine compound with an aldehyde selected from the group consisting of formaldehyde and paraformaldehyde and a secondary amine of the formula $HN(R')_2$ wherein $R'$ is the same or different group selected from the group consisting of lower alkyl, lower hydroxyalkyl, lower alkenyl, phenyl lower alkyl and lower cycloalkyl lower alkyl, and where the covalent bonding of the R's together with the nitrogen form a cyclic secondary amine, to yield a substituted aminomethyl compound of the formula

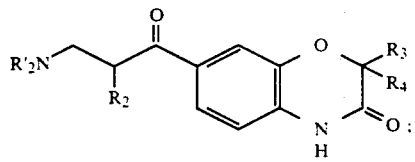

(e) alkylating the resultant substituted aminomethyl compound with an alkylating agent of the formula RL wherein R is $C_{1-6}$ straight-chain or branched alkyl and $C_{3-6}$ cycloalkyl, and L is selected from the group consisting of halo, —OS(O)Cl and —O-SO$_3$R wherein R is as defined above, to yield a quarternary ammonium compound of the formula

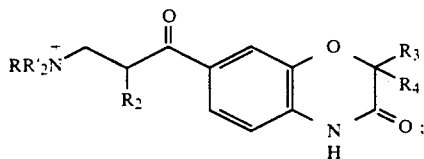

(f) reacting the resultant quaternary ammonium compound with an alkali metal cyanide to yield a nitrile compound of the formula

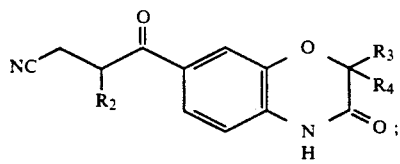

(g) hydrolyzing under acidic conditions the resultant nitrile compound to yield a carboxylic acid compound of the formula

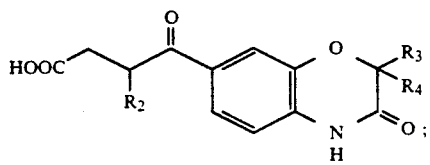

(h) reacting the resultant carboxylic acid compound with an alkali metal base in a solvent and then adding an alkylating agent of the formula $R_5L_2$ to the solvent wherein $R_5$ is as defined above except for H, $L_2$ is selected from the group consisting of halo, —OS(O)Cl and —OSO$_3$R$_5$ wherein $R_5$ is as defined above except for H, to yield an N-(alkyl) derivative of an ester compound of the formula

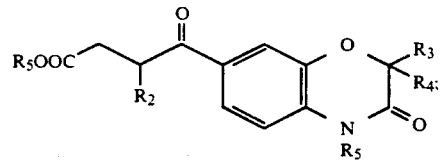

and (i) reacting the resultant N-(alkyl) derivative of the ester compound with a hydrazine derivative of the formula $R_1$ HN—NH$_2$, wherein $R_1$ is as defined above and provided where $R_1$ is other than H, the hydrazine nitrogen is bonded to a carbon in $R_1$ other than an unsaturated carbon.

16. The process of claim 15 wherein said alkanoic anhydride is selected from the group consisting of acetic anhydride and propionic anhydride.

17. The process of claim 15 wherein said 2-haloalkanoyl halide is selected from the group consisting of chloroacetyl chloride, 2-chloropropionyl chloride and 2-chloro-2-methyl-propionyl chloride.

18. The process of claim 15 wherein said secondary amine is selected from the group consisting of diethylamine, morpholine, dimethylamine, tetrahydroisoquinoline, diethanolamine, diallylamine, dibenzylamine, piperidine and isopropylmethylamine.

19. The process of claim 18 wherein said secondary amine is dimethylamine.

20. The process of claim 15 wherein said alkylating agent of step (e) is methyl iodide.

21. The process of claim 15 wherein said alkali metal cyanide is potassium cyanide.

22. The process of claim 15 wherein said alkylating agent of step (h) is methyl iodide.

23. A Process for preparing a compound of the formula

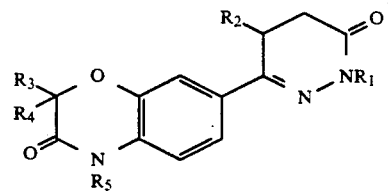

wherein $R_1$ is $C_{1-6}$ straight-chain alkyl, $C_{1-6}$ branched-chain alkyl, $C_{3-6}$ cycloalkyl or $C_{3-6}$ alkenyl;

$R_2$, $R_3$ and $R_4$ each is selected from the group consisting of H, $C_{1-6}$ straight-chain alkyl, $C_{1-6}$ branched-chain alkyl and $C_{3-6}$ cycloalkyl; and $R_5$ is selected from the group consisting of $C_{1-6}$ straight-chain alkyl, $C_{1-6}$ branched-chain alkyl and $C_{3-6}$ cycloalkyl, provided that the 2-nitrogen of the pyridazinone moiety is bonded to a carbon in $R_1$ other than an unsaturated carbon, which comprises the steps of:

(a) acylating 2-benzoxazolinone with an alkanoic anhydride of the formula (R₂CH₂CO)₂O, wherein R₂ is as defined above, in the presence of Eaton's reagent to yield an acylated carbamate compound of the formula

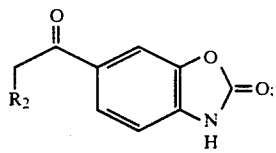

(b) hydrolyzing the resultant acylated carbamate under basic conditions to yield an aminophenol compound of the formula

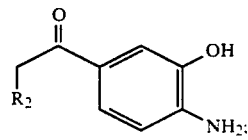

(c) reacting the resultant aminophenol compound with a 2-haloalkanoyl halide of the formula XR₃R₄CCOX, wherein R₃ and R₄ are as defined above and X is selected from the group consisting of chloro, bromo and iodo to yield a benzoxazine compound of the formula

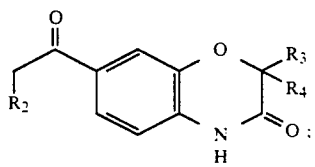

(d) reacting the resultant benzoxazine compound with an aldehyde selected from the group consisting of formaldehyde and paraformaldehyde and a secondary amine of the formula HN(R')₂ wherein R' is the same or different group selected from the group consisting of lower alkyl, lower hydroxyalkyl, lower alkenyl, phenyl lower alkyl and lower cycloalkyl lower alkyl, and where the covalent bonding of the R's together with the nitrogen form a cyclic secondary amine, to yield a substituted aminomethyl compound of the formula

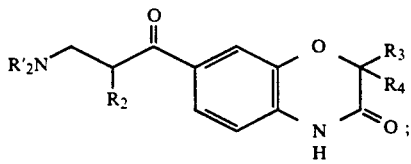

(e) alkylating the resultant substituted aminomethyl compound with an alkylating agent of the formula RL wherein R is C₁₋₆ straight-chain or branched alkyl and C₃₋₆ cycloalkyl, and L is selected from the group consisting of halo, —OS(O)Cl and —OSO₃R wherein R is as defined above, to yield a quarternary ammonium compound of the formula

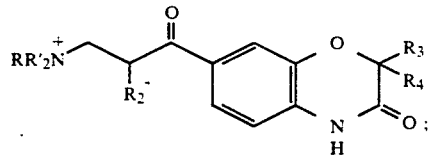

(f) reacting the resultant quaternary ammonium compound with an alkali metal cyanide to yield a nitrile compound of the formula

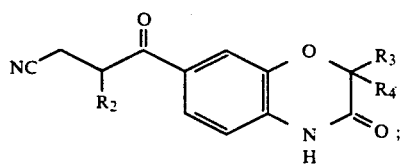

(g) hydrolyzing under acidic conditions the resultant nitrile compound to yield a carboxylic acid compound of the formula

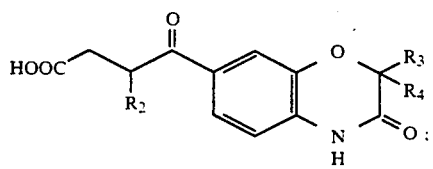

(h) reacting the resultant carboxylic acid compound with an alkali metal base in a solvent and then adding an alkylating agent of the formula R₅L₂ to the solvent wherein R₅ is as defined above except for H, L₂ is selected from the group consisting of halo, —OS(O)Cl and —OSO₃R₅ wherein R₅ is as defined above except for H, to yield an N-(alkyl) derivative of an ester compound of the formula

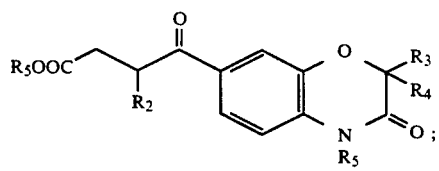

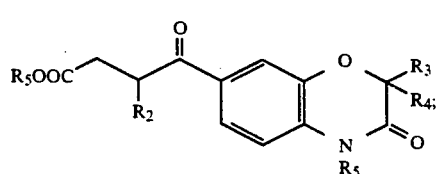

(i) reacting the resultant N-(alkyl) derivative of the ester compound with hydrazine to yield an N-(alkyl) 6-(3,4-dihydro-3-oxo-1,4(2H)-benzoxazin-7-yl)-2,3,4,5-tetrahydropyridazin-3-one compound of the formula

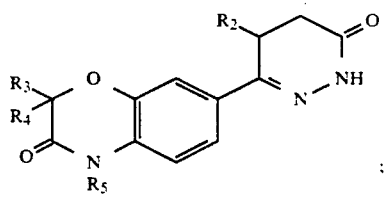

and (j) reacting the resultant N-(alkyl) 6-(3,4-dihydro-3-oxo-1,4(2H)-benzoxazin-7-yl)-2,3,4,5-tetrahydropyridazin-3-one compound with an alkali metal base in a solvent and then adding an alkylating agent of the formula $R_1 L_1$ to the solvent wherein $R_1$ is as defined above except for H, $L_1$ is selected from the group consisting of halo, —OS(O)Cl and —OSO$_3$R$_1$ wherein $R_1$ is as defined above except for H and $L_1$ is bonded to a carbon in $R_1$ other than an unsaturated carbon.

24. The process of claim 23 wherein said alkanoic anhydride is selected from the group consisting of acetic anhydride and propionic anhydride.

25. The process of claim 23 wherein said 2-haloalkanoyl halide is selected from the group consisting of chloroacetyl chloride, 2-chloropropionyl chloride and 2-chloro-2-methyl-propionyl chloride.

26. The process of claim 23 wherein said secondary amine is selected from the group consisting of diethylamine, morpholine, dimethylamine, tetrahydroisoquinoline, diethanolamine, diallylamine, dibenzylamine, piperidine and isopropylmethylamine.

27. The process of claim 26 wherein said secondary amine is dimethylamine.

28. The process of claim 23 wherein said alkylating agent of step (e) is methyl iodide.

29. The process of claim 23 wherein said alkali metal cyanide is potassium cyanide.

30. A process for preparing a compound of the formula

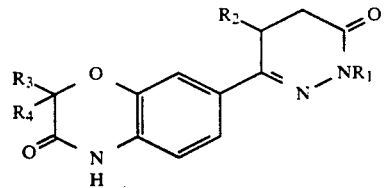

wherein
$R_1$ is selected from the group consisting of H, $C_{1-6}$ straight-chain alkyl, $C_{1-6}$ branched-chain alkyl, $C_{3-6}$ cycloalkyl and $C_{3-6}$ alkenyl; and
$R_2$, $R_3$ and $R_4$ each is selected from the group consisting of H, $C_{1-6}$ straight-chain alkyl, $C_{1-6}$ branched-chain alkyl and $C_{3-6}$ cycloalkyl, provided that where $R_1$ is other than H, the 2-nitrogen of the pyridazinone moiety is bonded to a carbon in $R_1$ other than an unsaturated carbon, which comprises the steps of:

(a) acylating 2-benzoxazolinone with an alkanoic anhydride of the formula $(R_2CH_2CO)_2O$, wherein $R_2$ is as defined above, in the presence of Eaton's reagent to yield an acylated carbamate compound of the formula

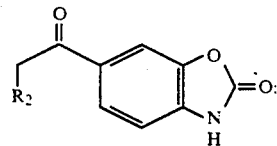

(b) hydrolyzing the resultant acylated carbamate under basic conditions to yield an aminophenol compound of the formula

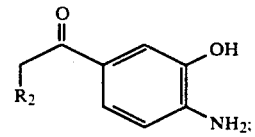

(c) reacting the resultant aminophenol compound with a 2-haloalkanoyl halide of the formula $XR_3R_4CCOX$, wherein $R_3$ and $R_4$ are as defined above and X is selected from the group consisting of chloro, bromo and iodo to yield a benzoxazine compound of the formula

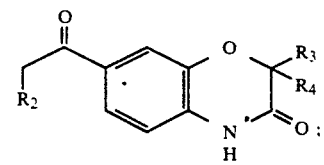

(d) reacting the resultant benzoxazine compound with an aldehyde selected from the group consisting of formaldehyde and paraformaldehyde and a secondary amine of the formula $HN(R')_2$ wherein R' is the same or different group selected from the group consisting of lower alkyl, lower hydroxyalkyl, lower alkenyl, phenyl lower alkyl and lower cycloalkyl lower alkyl, and where the covalent bonding of the R's together with the nitrogen form a cyclic secondary amine, to yield a substituted aminomethyl compound of the formula

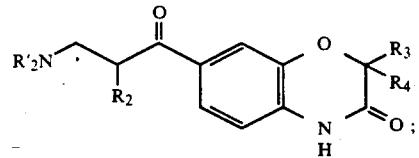

(e) alkylating the resultant substituted aminomethyl compound with an alkylating agent of the formula RL wherein R is $C_{1-6}$ straight-chain or branched alkyl and $C_{3-6}$ cycloalkyl, and L is selected from the group consisting of halo, —OS(O)Cl and —OSO$_3$R wherein R is as defined above, to yield a quaternary ammonium compound of the formula

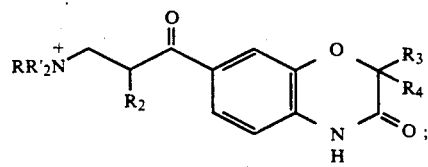

(f) reacting the resultant quaternary ammonium compound with an alkali metal cyanide to yield a nitrile compound of the formula

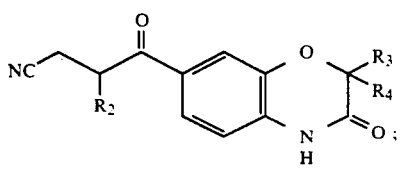

(g) hydrolyzing under acidic conditions the resultant nitrile compound to yield a carboxylic acid compound of the formula

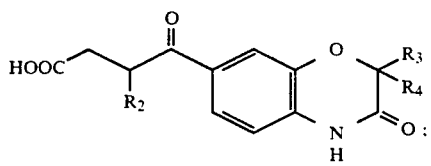

(h) esterifying under acidic conditions the resultant carboxylic acid compound to yield a corresponding ester; and (i) reacting the resultant ester compound with a hydrazine derivative of the formula $R_1HN-NH_2$, wherein $R_1$ is as defined above and provided where $R_1$ is other than H, the hydrazine nitrogen is bonded to a carbon in $R_1$ other than an unsaturated carbon.

31. The process of claim 30 wherein said alkanoic anhydride is selected from the group consisting of acetic anhydride and propionic anhydride.

32. The process of claim 30 wherein said 2-haloalkanoyl halide is selected from the group consisting of chloroacetyl chloride, 2-chloropropionyl chloride and 2-chloro-2-methylpropionyl chloride.

33. The process of claim 30 wherein said secondary amine is selected from the group consisting of diethylamine, morpholine, dimethylamine, tetrahydroisoquinoline, diethanolamine, diallylamine, dibenzylamine, piperidine and isopropylmethylamine.

34. The process of claim 33 wherein said secondary amine is dimethylamine.

35. The process of claim 30 wherein said alkylating agent of step (e) is methyl iodide.

36. The process of claim 30 wherein said alkali metal cyanide is potassium cyanide.

37. A process for preparing a compound of the formula

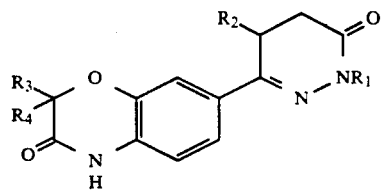

wherein
$R_1$ is $C_{1-6}$ straight-chain alkyl, $C_{1-6}$ branched-chain alkyl, $C_{3-6}$ cycloalkyl or $C_{3-6}$ alkenyl; and
R $R_3$, and $R_4$ each is selected from the group consisting of H, $C_{1-6}$ straight-chain alkyl, $C_{1-6}$ branched-chain alkyl and $C_{3-6}$ cycloalkyl, provided that the 2-nitrogen of the pyridazinone moiety is bonded to a carbon in $R_1$ other than an unsaturated carbon, which comprises the steps of:

(a) acylating 2-benzoxazolinone with an alkanoic anhydride of the formula $(R_2CH_2CO)_2O$, wherein $R_2$ is as defined above, in the presence of Eaton's reagent to yield an acylated carbamate compound of the formula

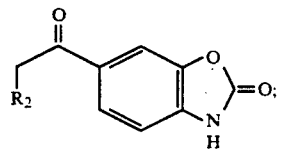

(b) hydrolyzing the resultant acylated carbamate under basic conditions to yield an aminophenol compound of the formula

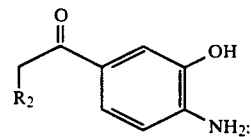

(c) reacting the resultant aminophenol compound with a 2-haloalkanoyl halide of the formula $XR_3R_4CCOX$, wherein $R_3$ and $R_4$ are as defined above and X is selected from the group consisting of chloro, bromo and iodo to yield a benzoxazine compound of the formula

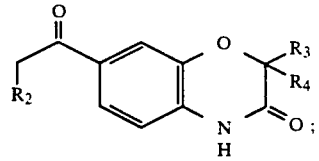

(d) reacting the resultant benzoxazine compound with an aldehyde selected from the group consisting of formaldehyde and paraformaldehyde and a secondary amine of the formula $HN(R')_2$ wherein R' is the same or different group selected from the group consisting of lower alkyl, lower hydroxyalkyl, lower alkenyl, phenyl lower alkyl and lower cycloalkyl lower alkyl, and where the covalent bonding of the R's together with the nitrogen form a cyclic-secondary amine, to yield a substituted aminomethyl compound of the formula

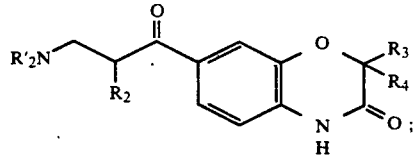

(e) alkylating the resultant substituted aminomethyl compound with an alkylating agent of the formula RL wherein R is $C_{1-6}$ straight-chain or branched alkyl and $C_{3-6}$ cycloalkyl, and L is selected from the group consisting of halo, —OS(O)Cl and —O-

SO₃R wherein R is as defined above, to yield a quarternary ammonium compound of the formula

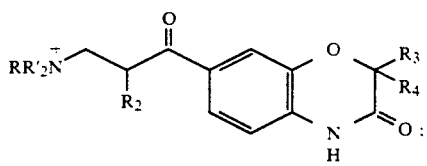

(f) reacting the resultant quaternary ammonium compound with an alkali metal cyanide to yield a nitrile compound of the formula

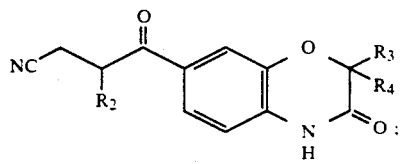

(g) hydrolyzing under acidic conditions the resultant nitrile compound to yield a carboxylic acid compound of the formula

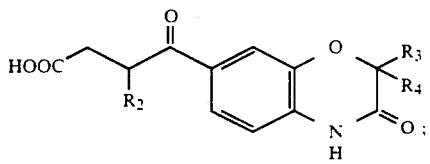

(h) esterifying under acidic conditions the resultant carboxylic acid compound to yield a corresponding ester;

(i) reacting the resultant ester compound with hydrazine to yield a 6-(3,4-dihydro-3-oxo-(2H)-1,4-benzoxazin-7-yl)-2,3,4,5-tetrahydropyridazin-3-one compound of the formula

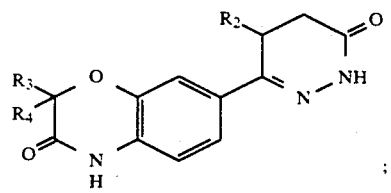

and (j) reacting the resultant 6-(3,4-dihydro-3-oxo-1,4(2H)-benzoxazin-7-yl)-2,3,4,5-tetrahydropyridazin-3-one compound with an alkali metal base in a solvent and then adding an alkylating agent of the formula $R_1L_1$ to the solvent wherein $R_1$ is as defined above except for H, $L_1$ is selected from the group consisting of a halo, —OS(O)Cl and —OSO₃R₁ wherein $R_1$ is as defined above except for H and $L_1$ is bonded to a carbon in $R_1$ other than an unsaturated carbon.

38. The process of claim 37 wherein said alkanoic anhydride is selected from the group consisting of acetic anhydride and propionic anhydride.

39. The process of claim 37 wherein said 2-haloalkanoyl halide is selected from the group consisting of chloroacetyl chloride, 2-chloropropionyl chloride and 2-chloro-2-methyl-propionyl chloride.

40. The process of claim 37 wherein said secondary amine is selected from the group consisting of diethylamine, morpholine, dimethylamine, tetrahydroisoquinoline, diethanolamine, diallylamine, dibenzylamine, piperidine and isopropylmethylamine.

41. The process of claim 40 wherein said secondary amine is dimethylamine.

42. The process of claim 37 wherein said alkylating agent of step (e) is methyl iodide.

43. The process of claim 37 wherein said alkali metal cyanide is potassium cyanide.

* * * * *